United States Patent [19]
Wagner

[11] Patent Number: 5,486,815
[45] Date of Patent: Jan. 23, 1996

[54] MOISTURE DETECTION CIRCUIT

[75] Inventor: Edward D. Wagner, Rogue River, Oreg.

[73] Assignee: Wagner Electronic Products, Inc., Rogue River, Oreg.

[21] Appl. No.: 9,274

[22] Filed: Jan. 26, 1993

[51] Int. Cl.⁶ .................................................. G08B 21/00
[52] U.S. Cl. ........................ 340/602; 340/604; 340/618; 324/664; 324/689; 73/304 C
[58] Field of Search ..................................... 340/602, 604, 340/618; 324/664, 689; 73/304 C

[56] References Cited

U.S. PATENT DOCUMENTS

| | | | |
|---|---|---|---|
| 3,967,197 | 6/1976 | Anderson | 324/664 |
| 4,683,418 | 7/1987 | Wagner et al. | 324/664 |
| 5,317,274 | 5/1994 | Nakagawa et al. | 324/664 X |

Primary Examiner—John K. Peng
Assistant Examiner—Edward Lefkowitz
Attorney, Agent, or Firm—Klarquist Sparkman Campbell Leigh & Whinston

[57] ABSTRACT

A detector circuit in a moisture detector having an oscillator, a detector electrode and a common electrode for measuring the moisture content of wood and structural materials in buildings comprises a clamping diode network which couples an AC signal generated in the oscillator to a detector electrode. The clamping network clamps the AC signal to a reference voltage. The clamping network is balanced by a second clamping diode network which, together with a low pass filter, establishes the reference voltage. A low pass filter connected to the first clamping network produces an output voltage signal related to the impedance between the electrodes. To maintain the circuit's stability, the diodes in the clamping networks are thermally coupled.

29 Claims, 2 Drawing Sheets

MOISTURE DETECTION CIRCUIT

FIELD OF THE INVENTION

The present invention relates to moisture detectors for measuring the moisture content of wood or structural materials of buildings, and more particularly relates to a detector circuit in such moisture detectors.

BACKGROUND OF THE INVENTION

One type of moisture detector for measuring the moisture content of wood uses an alternating current (AC) signal. The AC signal is generated by an oscillator circuit in the moisture detector and drives a detector circuit. This type of moisture detector also includes a sensor connected to the detector circuit which comprises a pair of electrodes, a detector electrode and a common electrode, that are typically plate-shaped. When the sensor is placed in close proximity to an object whose moisture is to be measured, the impedance between the electrodes is related to the moisture content of the wood. The impedance between the electrodes is sensed by the detector circuit using the AC signal to determine the moisture content of the object.

In one known prior moisture detector, a detector circuit is used that includes a transformer to couple the AC signal to the detector electrode. Generally, with a transformer, the circuit must be manually assembled, resulting in a more costly manufacturing or assembly process. Also, transformers are expensive circuit components. Therefore, because of the transformer, the cost of the detector circuit is considerably more than it would otherwise be.

It is therefore an object of the present invention to provide an improved moisture detector for detecting the moisture content of wood or other structural materials.

It is another object of the invention to provide such a moisture detector for detecting the moisture content of roofs or walls or other building components.

Yet another object of the invention is to provide an improved moisture detector circuit for use in moisture detectors that does not require a transformer.

It is a further object to provide a detector circuit that can be machine assembled and is constructed of relatively inexpensive components.

SUMMARY OF THE INVENTION

The present invention provides a detector circuit for moisture detectors that can be constructed of circuit components of the type which may be fabricated as on an integrated circuit. In accordance with a first aspect of the invention, the detector circuit comprises a clamping network which, in the preferred embodiment, is formed with a capacitor, a resistor, and a diode. The clamping network operates to shift the voltage level of the AC signal driving the detector electrode relative to a reference voltage at a reference voltage node.

In accordance with a further aspect of the invention, a low pass filter is connected between the detector electrode and the common electrode. The low pass filter forms a voltage signal at an output node equal to the average DC voltage level of the AC signal at the detector electrode. This voltage signal at the output node is related to the impedance between the detector electrode and the common electrode, and thus is related to the moisture content of the object being measured.

A drawback to this basic form of the invention is that the performance of the diode varies in relation to temperature. In accordance with yet a further aspect of the invention, the detector circuit is made insensitive to temperature using a second clamping network and a second low pass filter which are balanced with the first clamping network and low pass filter.

The second clamping network and second low pass filter set the voltage at the reference voltage node. In the preferred embodiment, the second clamping network is formed with a capacitor connected in series with a resistor between the AC signal output of the oscillator and a network node. A diode is connected between the network node and the common electrode. The second clamping network operates to level shift the AC signal at the network node. The second low pass filter in the preferred embodiment comprises a resistor connecting the network node and the reference voltage node, and a capacitor connecting the reference voltage node and the common electrode. Together, the second clamping network and low pass filter produce a reference voltage at the reference voltage node equal to the average voltage level of the level shifted AC signal at the network node.

The amount of level shifting produced by the clamping networks is dependent on the values of the components of the networks. The direction of the level shift is dependent on the orientation of the diode. When the component values of the two networks are matched and the diodes have opposite orientations, the detector circuit is balanced. More specifically, the second clamping network shifts the DC level of the signal at the network node by some amount in one direction relative to the voltage at the common electrode. With the second low pass filter, the voltage at the reference voltage node is equal to the level shift produced by the second clamping network. The first clamping network shifts the signal at the detector electrode an equal amount in the opposite direction relative to the voltage at the reference voltage node. Thus, when balanced, the voltage at the output node which is equal to the average voltage level of the detector electrode signal is approximately equal to the voltage at the common electrode. However, changing the impedance between the electrodes such as by placing the electrodes adjacent to a moisture containing object, unbalances the detector circuit and causes a voltage related to the moisture content of the object to be generated at the output node.

Since the performance of the diodes is sensitive to temperature, the detector circuit balance can be upset if the diodes are subjected to differing temperatures. In the present invention, the detector circuit is made temperature insensitive by thermally coupling the diodes of the clamping networks. The performance of the diodes are then equally affected by temperature change, and the detector circuit remains balanced.

The foregoing and additional features, objects, and advantages of the invention will be more readily apparent from the following detailed description, which proceeds with reference to the accompanying drawings.

DETAILED DESCRIPTION OF THE PREFERRED EMBODIMENT

Figure 1:
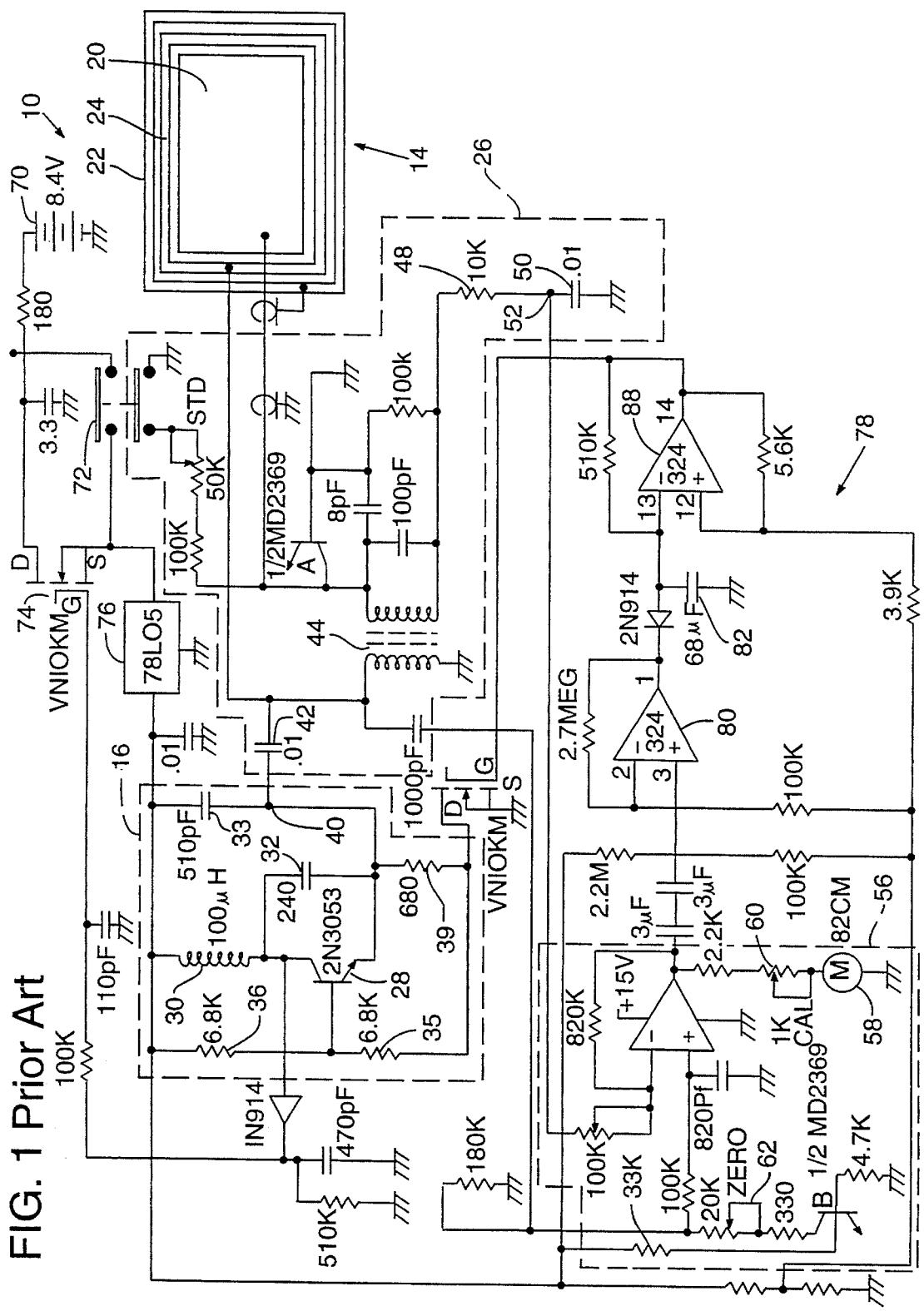
FIG. 1 is a schematic diagram of a moisture detector circuit of the prior art.

With reference to FIG. 1, a prior art moisture detector 10 comprises a sensor 14 which is driven with an AC signal generated by an oscillator circuit 16. The sensor 14 includes three plate-shaped electrodes: a detector electrode 20, a common electrode 22, and a transmitter electrode 24. The detector electrode 20 is shaped as a rectangular plate of conductive material. The transmitter electrode 24 is a flat strip of conductive material around the circumference of the detector electrode 20 and separated therefrom by a small spacing. The common electrode 22 surrounds and is spaced apart from the transmitter electrode 24. All three electrodes 20–24 are in the same plane. Typically, the electrodes 20–24 are formed by plating one surface of a fiberglass circuit board material with copper and then etching or otherwise separating the copper plating to form concentric rectangular plates.

When the sensor 14 is placed in close proximity to an object such as wood or structural materials of buildings, the impedance between the detector electrode 20 and the common electrode 22 is inversely related to the moisture content of the object. To sense the moisture content of the object, the moisture detector further includes a detector circuit 26 which produces a voltage signal related to the impedance between the detector electrode 20 and the common electrode 22, and hence related to the moisture content of the object.

The detector circuit 26 senses the impedance between the electrodes 20, 22 by coupling the AC signal of the oscillator circuit 16 to the detector electrode 20. The oscillator circuit 16 comprises a transistor 28, an inductor 30, capacitors 32–33, and resistors 34–36 in a Colpitts oscillator configuration and generates the AC signal at an oscillator node 40. The AC signal at the oscillator node 40 is coupled to the detector electrode 20 through a capacitor 42 and a transformer 44 in the detector circuit 26. The voltage level of the AC signal at the transformer 44 depends, in part, on the impedance between the electrodes 20, 22, and is thus related to the moisture content of the object being measured.

The detector circuit also includes a low pass filter consisting of a resistor 48 and a capacitor 50. The low pass filter filters the AC signal at the transformer 44 to produce, at a node 52 between the resistor 48 and the capacitor 50, a voltage signal related to the moisture content. The voltage signal formed at the node 52 drives a gain circuit 56. The gain circuit 56 increases the magnitude of the voltage signal in order to drive a meter 58 which registers the detected moisture content of the object. The meter 58 can be calibrated and zeroed prior to performing a measurement using variable resistors 60, 62, respectively, in the gain circuit 56.

The transmitter electrode 24 of the sensor 14 is also driven with the AC oscillator signal. This causes the impedance path of the AC signal between the detector electrode 20 and the common electrode 22 to penetrate deeper into the object whose moisture content is being measured, yielding a more accurate measurement of the moisture content within the object. One advantage of the transmitter electrode 24 when operated in this manner, is that surface moisture on the object can be ignored by the moisture detector 10 when measuring the moisture content of the object.

The remaining circuitry in the moisture detector 10 operate to turn the moisture detector on and off. A battery 70 provides power to the moisture detector. The moisture detector is turned on with a switch 72, and maintained "on" with an on/off transistor 74. A switching power supply circuit 76 powered by the battery 70 through the on/off transistor 74 provides the proper power voltages required for circuit operation. While the moisture detector is in use, a voltage at the gate 77 of the on/off transistor keeps current flowing to the circuit. However, after non-use of the moisture detector 10 for approximately 90 seconds, the moisture detector is shut-off by an automatic shut-off circuit 78.

The automatic shut-off circuit 78 is basically a motion detector circuit which senses movement of the voltage signal which drives the meter 58 in the gain circuit 56. An amplifier circuit 80 in the automatic shut-off circuit 78 is also driven with the voltage signal from the gain circuit 56. When the moisture detector is in use, the voltage signal fluctuates and the amplifier circuit 80 charges a capacitor 82. When the moisture detector is not in use, the amplifier circuit 80 discharges the capacitor 82 in approximately the 90 second shut-off period. When the capacitor 82 is discharged, a second amplifier circuit 88 in the automatic shut-off circuit 56 turns off the oscillator circuit 16. When the oscillator circuit is turned off, the on/off transistor 74 shuts off the power from the battery 70.

Figure 2:
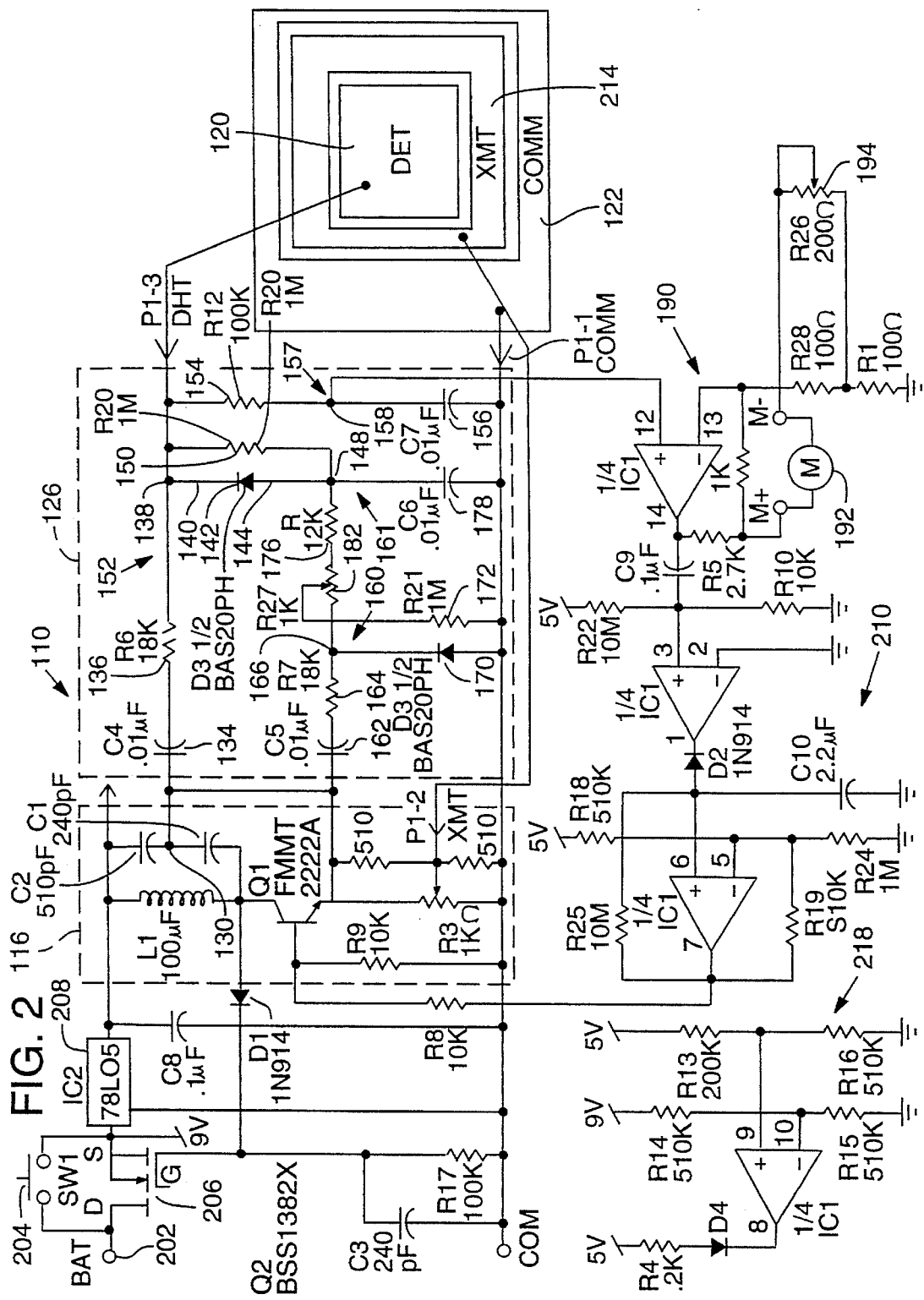
FIG. 2 is a schematic diagram of a detector circuit for a moisture detector in accordance with a preferred embodiment of the present invention.

In a preferred embodiment of the present invention, a moisture detector 110 shown in FIG. 2 comprises an oscillator circuit 116, a detector electrode 120, a common electrode 122 and a detector circuit 126. The oscillator circuit 116 may be of any suitable type with one example being an LC Colpitts-type oscillator which produces an AC signal of approximately 1.2 MHz at an oscillator node 130. The detector and common electrodes 120, 122 are preferably configured as in the sensor 14 of the prior art moisture detector 10.

The detector circuit 126 comprises a capacitor 134 and a resistor 136 connected in series between the oscillator node 130 and the detector electrode 120 so that the detector electrode is driven by the AC signal. At a node 138 where the resistor 136 is connected to the detector electrode 120, an anode 140 of a diode 142 is connected. A cathode 144 of the diode 142 is connected to a reference voltage node 148. Preferably, a bleed resistor 150 is also connected between the node 138 and the reference voltage node 148.

The capacitor 134, resistor 136, and diode 142 in this configuration form a clamping network 152. The clamping network 152 operates to shift the AC signal at the node 138 relative to a reference voltage at the reference voltage node 148. More specifically, with the anode 140 of the diode 142 connected to the node 138 and the cathode 144 connected to the reference voltage node 148, the clamping network 152 shifts the voltage level of the AC signal at the node 138 so that the maximum peak voltage of the signal is clamped to the reference voltage.

The detector circuit 126 also comprises a resistor 154 and a capacitor 156 connected in series between the detector electrode 120 and the common electrode 122. The resistor 154 and the capacitor 156 form a low pass filter 157 which produces a voltage signal at an output node 158 (at the juncture of the resistor 154 and the capacitor 156) equal to the average voltage level of the AC signal at the node 138. The average voltage level of the AC signal driving the detector electrode 120 is dependent on the impedance between the electrodes 120, 122 and on the reference voltage (since the AC signal is clamped to the reference voltage with the clamping network 152). When the electrodes 120, 122 are placed in close proximity to a moisture containing object, the impedance between the electrodes varies in relation to the moisture content of the object. Thus, the voltage signal produced at the output node 158 is related to the moisture content of the object.

The detector circuit 126 comprises a further clamping network 160 and low pass filter 161 for producing the reference voltage at the reference voltage node 148. The clamping network 160 comprises a capacitor 162 and a resistor 164 connected in series between the oscillator node 130 and a network node 166. The network 160 also comprises a diode 170 and a bleed resistor 172 each connected between the network node 166 and the common electrode 122. The diode 170 has its anode connected to the common electrode 122 and its cathode connected to the network node 166. With the diode 170 connected in this manner, the AC signal at the network node 166 is level shifted relative to the voltage at the common electrode 122 in a direction opposite the level shifting of the AC signal at the node 138. More specifically, the AC signal is shifted so that its minimum peak is clamped to the voltage at the common electrode. In the preferred embodiment, the common electrode is at ground voltage. The AC signal is thus shifted so that its minimum voltage peak is clamped to the ground voltage.

The low pass filter 161 comprises a resistor 176 and a capacitor 178. The resistor 176 couples the network node 166 to the reference voltage node 148. The capacitor 178 connects the reference voltage node 148 to the common electrode 122. This produces a voltage (the reference voltage) at the reference voltage node 148 equal to the average voltage level of the level shifted AC signal at the network node 166. In the preferred embodiment, the reference voltage is approximately +3 Volts.

The component values of the clamping networks 152, 160 and low pass filters 157, 161 are preferably matched to balance the detector circuit 126. More specifically, the values of the capacitor 134, resistor 136, and bleed resistor 150 of the clamping network 152 are matched to the values of the capacitor 162, resistor 164, and bleed resistor 172 in the clamping network 160, respectively. The values of the capacitors 156, 178 in the low pass filters 157, 161 are also matched. For the detector circuit 126 to be balanced, the impedance between the electrodes 120, 122 should also be matched to the resistance between the network node 166 and the reference voltage node 148. A potentiometer 182 is therefore connected in series with the resistor 176 between the network node 166 and the reference voltage node 148 and can be adjusted to match the impedance between the electrodes.

When the detector circuit 126 is balanced, the voltage at the output node 158 is approximately equal to the voltage at the common electrode or ground. Both of the clamping networks 152, 160 in the detector circuit 126 are driven with the same AC signal generated at the oscillator node 130. In the clamping network 160, the AC signal at the network node 166 is level shifted relative to the voltage at the common electrode 122 so that the minimum peak of the signal is clamped at the common electrode voltage. The reference voltage produced by the low pass filter 161 at the reference voltage node 166 is equal to the average voltage level of this AC signal at the network node 166 or approximately +3 Volts. In the clamping network 152, however, the AC signal at the node 138 is level shifted relative to the reference voltage in the opposite direction so that the maximum peak of the AC signal is clamped to the reference voltage. Since the AC signals have the same peak to peak amplitude, the average voltage level of the AC signal will be approximately equal to the voltage at the common electrode 122 or ground voltage.

The voltage signal at the output node 158 of the low pass filter 157 is equal to the average voltage level of the AC signal at the node 138. When the detector circuit 126 is balanced, the voltage signal is at ground voltage. The balance of the detector circuit 126, however, can be upset by varying the impedance between the detector and common electrodes 120, 122. The impedance between the electrodes varies in relation to the moisture content of objects in the proximity of the electrodes. If an object adjacent to the electrodes has a high moisture content, for example, the impedance is relatively low. If, however, the object has a low moisture content, the impedance is much higher. The detector circuit 126 is preferably adjusted with the potentiometer 182 to yield a voltage signal at ground voltage when the electrodes are not in the proximity of moisture. The potentiometer thus operates to zero the voltage signal.

The voltage signal at the output node 158 drives a gain circuit 190. The gain circuit 190 amplifies the voltage to drive a meter 192. The gain of the circuit can be adjusted with a potentiometer 194 to scale the amplitude of the voltage signal, and thus calibrate the voltage signal. The meter 192 includes a needle which is deflected across a dial to indicate the amplitude of the voltage. The dial is scaled to read the percentage moisture content.

To insure the stability of the detector circuit 126, the diodes 142, 170 preferably have a common thermal connection. In the preferred embodiment, for example, the diodes 142, 170 are formed on a common substrate of a semiconductor chip. Alternatively, the diodes can be separate components which are attached to a common heat sink or otherwise tied together so as to operate at the same temperature. When the diodes are thermally coupled in this manner, the performance of the clamping networks remains balanced regardless of the operating temperatures of the circuits.

Like the prior art moisture detector 10, the moisture detector 110 used with preferred embodiment of the detector circuit 126 of present invention includes a battery 202, a switch 204, and on/off transistor 206, a power circuit 208, and an automatic shut-off circuit 210. The moisture detector 110 also includes a transmitter electrode 214 driven by an AC signal generated in the oscillator circuit 116. The transmitter electrode 214, when driven with the AC signal, operates to increase the depth of penetration of the AC signal driving the detector electrode 120. The moisture detector also includes a low battery indicator circuit 218.

Having described and illustrated the principles of my invention with reference to a preferred embodiment thereof, it will be apparent that the invention can be modified in arrangement and detail without departing from such principles. In view of the many possible embodiments to which the principles of my invention may be put, it should be recognized that the detailed embodiment is illustrative only and should not be taken as limiting the scope of my invention. Accordingly, I claim as my invention all such modifications as may come within the scope and spirit of the following claims and equivalents thereto.

I claim:

1. A moisture detector comprising:

an oscillator having an AC signal output;

a common electrode;

a detector electrode for placing in proximity to an object such that an impedance between the detector electrode and the common electrode is related to a moisture content of the object;

a first capacitor and a first resistor connected in series between the AC signal output of the oscillator and the detector electrode for driving the detector electrode with an AC signal which is affected by the impedance between the detector electrode and the common electrode such that a voltage level of the AC signal is thereby related to the moisture content of the object; and a first diode connected between the detector electrode and a reference voltage node, whereby the voltage at the detector electrode is level shifted relative to a reference voltage at the reference voltage node.

2. The moisture detector of claim 1 further comprising:

a filter resistor and a filter capacitor connected in series between the detector electrode and the common electrode to form a low pass filter whereby a moisture content signal is formed at a juncture of the filter resistor and the filter capacitor.

3. The moisture detector of claim 1 further comprising:

a common electrode;

a second capacitor and a second resistor connected in series between the AC signal output of the oscillator and the reference voltage node; and a second diode connected between the common electrode and the reference voltage node, whereby the voltage at the reference voltage node is level shifted relative to the common electrode, the level shifting at the reference voltage node being opposite the level shift of the voltage at the detector electrode.

4. The moisture detector of claim 3 further comprising:

a bleed resistor connected in parallel with the first diode; and a second bleed resistor connected in parallel with the second diode.

5. The moisture detector of claim 3 wherein the diodes have a common thermal connection.

6. The moisture detector of claim 5 wherein the diodes are formed on a common substrate of a semiconductor device.

7. The moisture detector of claim 3 comprising:

a resistor and a capacitor connected in series between the detector electrode and the common electrode to form a low pass filter whereby a moisture content signal is formed at a juncture of the resistor and the capacitor.

8. The moisture detector of claim 3 comprising:

a resistor connected between the reference voltage node and a juncture of the second resistor and the second diode; and a capacitor connected between the reference voltage node and the common electrode, whereby a reference voltage is produced at the reference voltage node.

9. The moisture detector of claim 3 for measuring the moisture content of wood and lumber.

10. The moisture detector of claim 3 for measuring the moisture content of structural materials in a building.

11. A detector circuit for a moisture detector comprising an oscillator, a detector electrode and a common electrode for placing in proximity to an object whereby an impedance between the electrodes is related to a moisture content of the object, the detector circuit comprising:

a first capacitor having a first and a second terminal, the first terminal being connected to an AC signal output of the oscillator;

a first resistor having a first terminal connected to the second terminal of the first capacitor and a second terminal connected to a first node, the first node being coupled to the detector electrode to drive the detector circuit with an AC signal having a voltage level affected by the impedance between the electrodes and thereby related to the moisture content of the object; and a first diode having a first terminal connected to the first node and a second terminal connected to a reference voltage node.

12. The detector circuit of claim 11 further comprising:

a second resistor having a first terminal connected to the first node and a second terminal connected to an output node; and a second capacitor having a first terminal connected to the output node and a second terminal connected to the common electrode, whereby a signal related to the moisture content of wood placed in close proximity to the electrodes is produced at the output node.

13. The detector circuit of claim 12 further comprising a bleed resistor having a first terminal connected to the first node and a second terminal connected to the reference voltage node.

14. The detector circuit of claim 12 further comprising:

a third capacitor having first and second terminals, the first terminal being connected to the output of the oscillator;

a third resistor having a first terminal connected to the second terminal of the third capacitor and a second terminal connected to a second node;

a second diode having a first terminal connected to the second node and a second terminal connected to the common electrode;

a fourth resistor having a first terminal connected to the second node and a second terminal connected to the reference voltage node; and a fourth capacitor having a first terminal connected to the reference voltage node and a second terminal connected to the common electrode, whereby a reference voltage is produced at the reference voltage node.

15. The detector circuit of claim 14 wherein the first diode has an anode connected to the first node and a cathode connected to the reference voltage node, and wherein the second diode has an anode connected to the common electrode and a cathode connected to the second node.

16. The detector circuit of claim 15 wherein the first diode has an cathode connected to the first node and an anode connected to the reference voltage node, and wherein the second diode has an cathode connected to the common electrode and an anode connected to the second node.

17. The detector circuit of claim 16 wherein the first and second diodes have a common thermal connection.

18. The detector circuit of claim 17 wherein the first and second diodes are formed on a common substrate of a semiconductor device.

19. The detector circuit of claim 18 further comprising a second bleed resistor having a first terminal connected to the second node and a second terminal connected to the common electrode.

20. The detector circuit of claim 19 wherein the first capacitor, first resistor, and first diode are matched in value to the third capacitor, third resistor, and second diode.

21. The detector circuit of claim 11 for measuring the moisture content of wood and lumber.

22. The detector circuit of claim 11 for measuring the moisture content of roofs, walls and other structural components of buildings.

23. A moisture detector comprising:

an oscillator for producing an AC signal at an output;

a common electrode;

a detector electrode for placing in proximity to an object whereby an impedance between the detector electrode and the common electrode is affected by a moisture content of the object; and a detector circuit for driving the detector electrode with the AC signal and applying a common voltage to the common electrode such that the AC signal is affected by the impedance between the detector electrode and the common electrode and thereby is related to the moisture content of the object, wherein the detector circuit comprises:

a first capacitor having a first and a second terminal, the first terminal being connected to the oscillator output;

a first resistor having a first terminal connected to the second terminal of the first capacitor and a second terminal connected to a first node, the first node being coupled to the detector electrode; and a first diode having a first terminal connected to the first node and a second terminal connected to a reference voltage node.

24. The moisture detector of claim 23 wherein the detector circuit further comprises:

a second resistor having a first terminal connected to the first node and a second terminal connected to an output node; and a second capacitor having a first terminal connected to the output node and a second terminal connected to the common electrode, whereby a signal related to the moisture content of wood placed in close proximity to the electrodes is produced at the output node.

25. The moisture detector of claim 23 wherein the detector circuit further comprises:

a second capacitor having first and second terminals, the first terminal being connected to the oscillator output;

a second resistor having a first terminal connected to the second terminal of the third capacitor and a second terminal connected to a second node;

a second diode having a first terminal connected to the second node and a second terminal connected to the common electrode;

a third resistor having a first terminal connected to the second node and a second terminal connected to the reference voltage node; and a third capacitor having a first terminal connected to the reference voltage node and a second terminal connected to the common electrode, whereby a reference voltage is produced at the reference voltage node.

26. The moisture detector of claim 25 wherein the first diode has an anode connected to the first node and a cathode connected to the reference voltage node, and wherein the second diode has an anode connected to the common electrode and a cathode connected to the second node.

27. The moisture detector of claim 25 wherein the first diode has an cathode connected to the first node and an anode connected to the reference voltage node, and wherein the second diode has an cathode connected to the common electrode and an anode connected to the second node.

28. The moisture detector of claim 25 wherein the first and second diodes have a common thermal connection.

29. The moisture detector of claim 25 wherein the first capacitor, first resistor, and first diode are matched in value to the second capacitor, second resistor, and second diode.

* * * * *